United States Patent

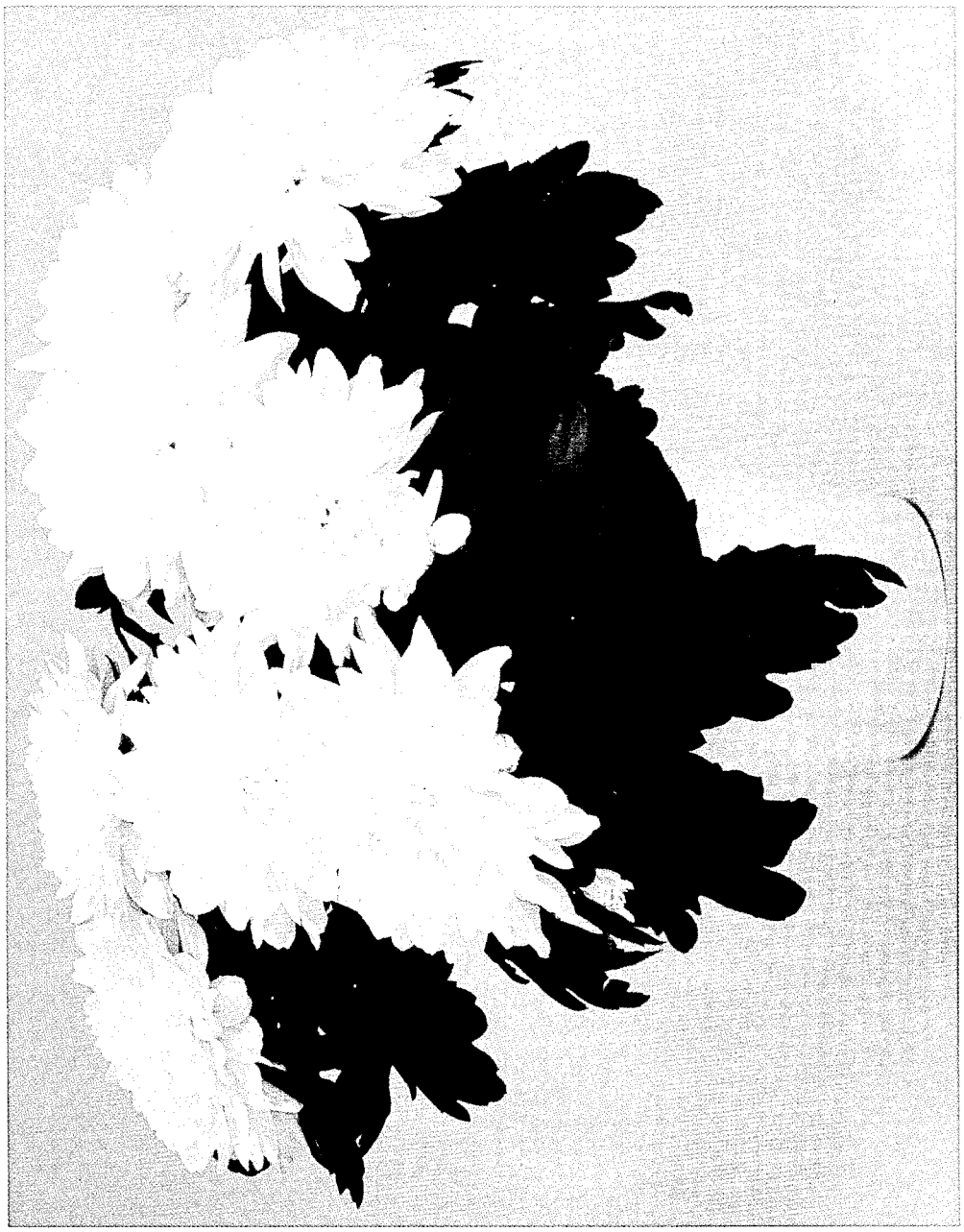

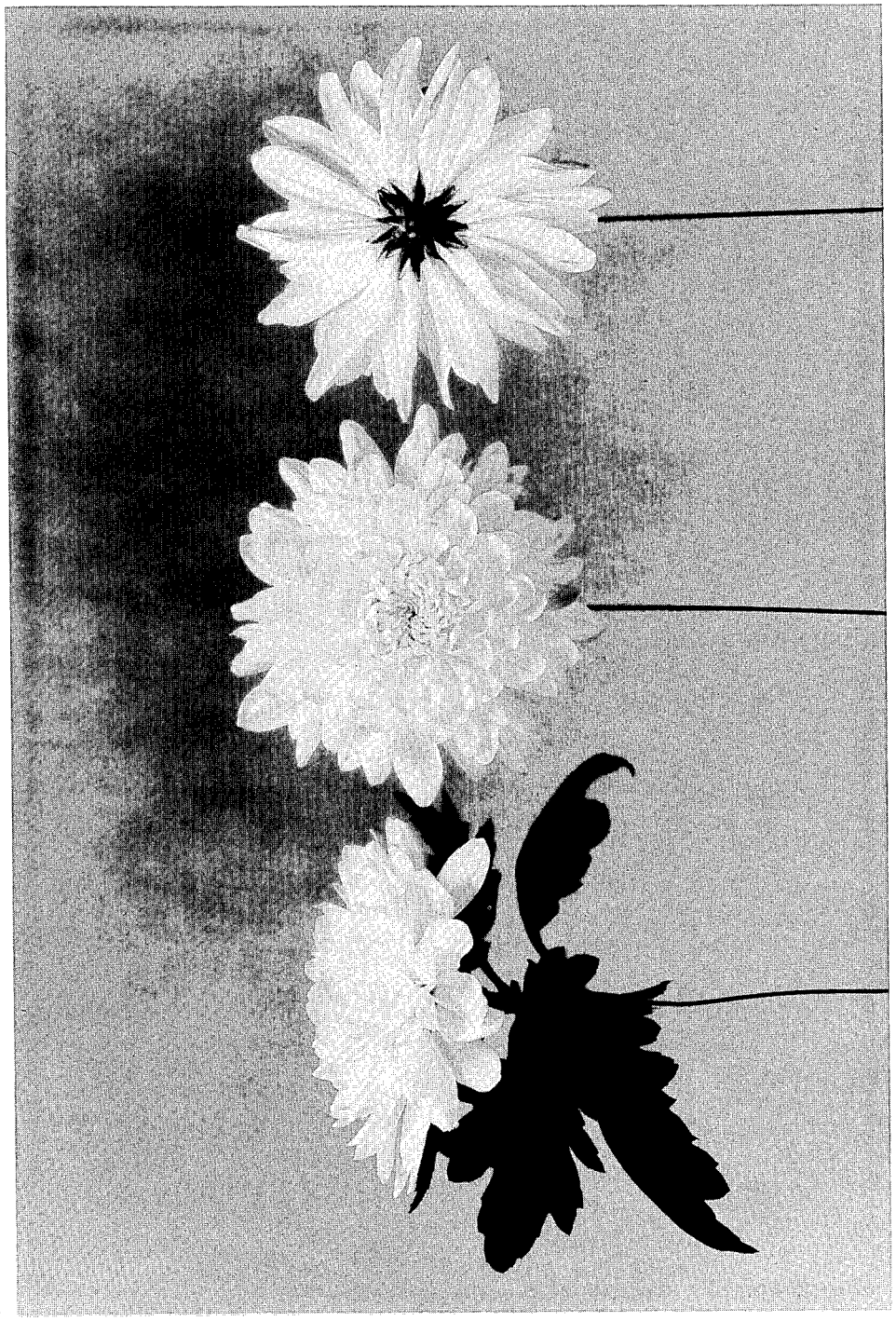

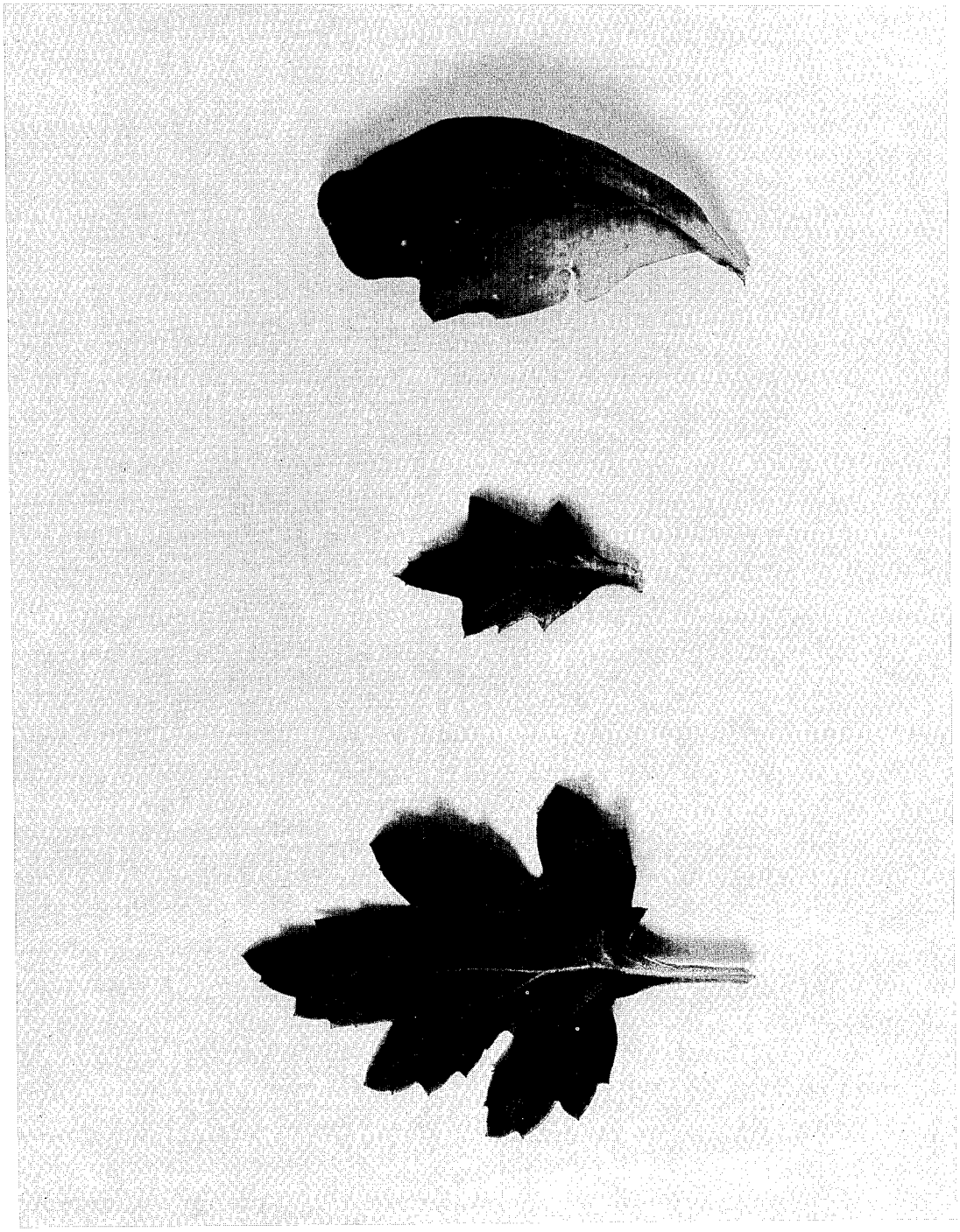

Plant Pat. 3,908

Patented June 15, 1976

3,908

CHRYSANTHEMUM PLANT

Walter H. Jessel, Jr., Doylestown, and William E. Duffett, Akron, Ohio, assignors to Yoder Brothers, Inc., Barberton, Ohio

Filed May 15, 1975, Ser. No. 577,921

Int. Cl. A01h *5/00*

U.S. Cl. Plt.—77 1 Claim

The present invention comprises a new and distinct cultivar of *Chrysanthemum morifolium,* Ramat., hereinafter referred to by the cultivar name, Intrepid White (#68146001).

Intrepid White was originated from a cross made in a controlled breeding program in Barberton, Ohio in the year 1967.

The female, or seed parent, was #65307001 (unnamed seedling), a light pink decorative originated by the present inventors from a cross between Princess Anne (#21560E02; unpatented; commercially available) and Orchid King (#21555001; unpatented; commercially available). Both Princess Anne and Orchid King are of parentage unknown to the present inventors.

The male, or pollen parent, was Mandalay (#6186-5001; unpatented; commercially available), a bronze decorative originated by the present inventors from a cross between Woking Scarlet (#21383001; unpatented; commercially available) and Mayford Crimson (#21402001; unpatented; commercially available). Both Woking Scarlet and Mayford Crimson are of parentage unknown to the present inventors.

Intrepid White was discovered and selected as a flowering seedling within the progeny of the stated cross by William E. Duffett and Walter H. Jessel, Jr., on Nov. 20, 1968 in a controlled environment in Barberton, Ohio.

Intrepid White is a product of a planned breeding program which had the objective of creating cultivars with decorative type inflorescence of medium to large size, with branching habit and plant height readily adaptable to pot mum culture, and with the ability to produce commercially acceptable quality in controlled flowering programs on a year round basis. These traits in combination were not previously available in commercial cultivars.

The first act of asexual reproduction of Intrepid White was accomplished when vegetative cuttings were taken from the initial selection in January 1967 in a controlled environment in Barberton, Ohio by a technician under formulations established and supervised by William E. Duffett and Walter H. Jessel, Jr. Horticultural examination of selected units initiated Nov. 19, 1969 has demonstrated that the combination of characteristics as herein disclosed for Intrepid White are firmly fixed and are retained through successive generations of asexual reproduction.

Intrepid White has not been observed under all possible environments. The phenotype may vary significantly with variations in environment such as temperature, light intensity, and daylength. The following observations, measurements, and comparisons describe pinched, disbudded plants grown in a greenhouse in Barberton, Ohio under environmental conditions which closely approximate those generally used in commercial practice, as described in Chart A and Chart B which appear at the end of the present specification.

The following traits have been repeatedly observed and are determined to be basic characteristics of Intrepid White which in combination distinguish this chrysanthemum as a new and distinct cultivar:

(1) Decorative inflorescence type.

(2) Flat inflorescence form.

(3) Diameter across face of inflorescence from 4.0 to 5.5 inches at maturity.

(4) Uniform eight week flowering response.

(5) Short plant height.

(6) Semi-upright branching habit.

(7) Adaptability to a wide range of container sizes due to responsiveness of height to daylength and B–9.

The accompanying photographic drawings show typical inflorescence and foliage characteristics of Intrepid White, with colors being as nearly true as possible with illustrations of this type. Sheet 1 is a color photograph of Intrepid White. Sheet 2 is a black and white photograph showing three different views of the inflorescence of Intrepid White, and Sheet 3 is a black and white photograph showing the foliage of Intrepid White at three stages of growth.

Of the many commercial cultivars known to the present inventors, the most similar existing cultivar in comparison to Intrepid White is Cream Yellow Princess Anne (#2156AE02, unpatented). Intrepid White may also be compared to Intrepid Gold (#68146D01; U.S. patent pending). Reference is made to attached Chart C which compares certain characteristics of the above mentioned cultivars with the same characteristics of Intrepid White. General comparisons are as follows:

(1) In comparison to Cream Yellow Princess Anne, Intrepid White has different inflorescence color, shorter plant height, shorter flowering response period, and smaller diameter across face of inflorescence. The branching habit and inflorescence form and type of Intrepid White are similar to those of Cream Yellow Princess Anne.

(2) In comparison to Intrepid Gold, Intrepid White has different inflorescence color and different inflorescence form. The diameter across face of inflorescence, plant height, branching habit, inflorescence type, and flowering response period of Intrepid White are similar to those of Intrepid Gold.

In the following description, color references are made to The Munsell Limit Color Cascade, 1972 edition. The color values were determined between 9:00 a.m. and 9:30 a.m. on Feb. 6, 1975 under 140 foot candle light intensity at Barberton, Ohio.

BOTANICAL CLASSIFICATION

*Chrysanthemum morifolium,* Ramat., cv Intrepid White

(*I*) *Inflorescence*

(A) Capitulum:

*Form.*—Flat.

*Type.*—Decorative.

*Pearmanence.*—10–12 days.

*Diameter across face.*—4.0 to 5.5 inches.

(B) Corolla of ray florets:
*Texture (adaxial).*—Glabrous.

*Veination.*—Prominent.
*Margin.*—Slightly serrated.

CHART A—AVERAGE GREENHOUSE CHRYSANTHEMUM ENVIRONMENTS USED FOR BARBERTON, OHIO

| Season | Temperatures used: Night | Bright day | Cloudy day | Lighting used | Black cloth used | Supp., $CO_2$ |
|---|---|---|---|---|---|---|
| Fall | 65 to 56 | 65 to 80 | 60 to 75 | 2 to 4 weeks at 3 hours per night of 7–10 f.c. | To Sept. 15: on, 5:30 p.m., off, 7:30 a.m. | From Oct. 15: 300 p.p.m. |
| Winter | 58 to 62 | 65 to 70 | 60 to 65 | 2 to 5 weeks at 5 hours per night of 7–10 f.c. | None | 300 p.p.m. |
| Spring | 58 to 65 | 65 to 80 | 60 to 75 | 2 to 4 weeks at 5 hours per night of 7–10 f.c. | From Mar. 15: on, 5:30 p.m.; off, 7:30 a.m. | To Apr. 15: 300 p.p.m. |
| Summer | 62 to 68 | 70 to 90 | 65 to 75 | 1 to 2 weeks at 3 hours per night of 7–10 f.c. | On, 6:00 p.m.; off, 8:00 a.m. | None. |

NOTE.—For intensity of direct solar radiation, refer to Chart B.

*Appearance and form.*—Ligulate.
*Arrangement.*—Whorled on receptacle.
*Persistance.*—Resists shatter.
*Color (abaxial).*—26–3 to white.
*Color (adaxial).*—26–4 (apex) to white.

(C) Reproductive organs:
*Androecium.*—Present disc florets only; syngenesious stamen; scant pollen.
*Gynoecium.*—Present both ray and disc florets; inferior, bicarpellate ovary; single style; 2-lobed stigma.

*(II) Plant*

(A) General appearance: Semi-upright; short.
(B) Duration and texture: Perennial; herbaceous.
(C) Foliage:
*Color (abaxial).*—20–15 to 20–13 with more grey.
*Color (adaxial).*—20–13 with more grey.
*Shape.*—Spatulate; moderately lobed.
*Texture.*—Glabrous.
*Arrangement.*—Alternate.

CHART B

INTENSITY OF DIRECT SOLAR RADIATION

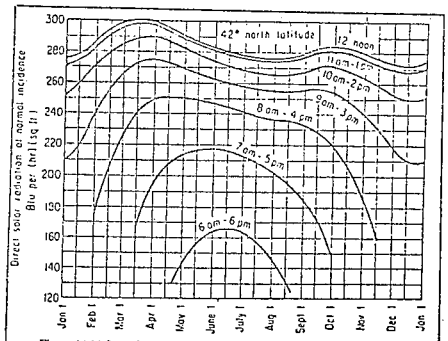

Figure 14.14 Intensity of direct solar radiation normal to the sun's rays at 42 degrees north latitude for an atmospheric clearness number of unity. (Reprinted by permission from *ASHAE Trans.*, Vol. 64, p. 64.)

CHART C—COMPARISON OF INTREPID WHITE WITH CREAM YELLOW PRINCESS ANNE AND INTREPID GOLD

| Cultivar | Inflorescence color | Diameter across face of inflorescence (inches) | Height | Branching habit | Flowering response period | Inflorescence form and type |
|---|---|---|---|---|---|---|
| Intrepid White | Ivory to white | 4.0 to 5.5 | Short | Semiupright | 8 | Flat decorative. |
| Cream Yellow Princess Anne | Light yellow to ivory | 4.75 to 5.75 | Very tall | do | 10 | Do. |
| Intrepid Gold | Golden yellow | 4.9 to 5.5 | Short | do | 8 | Semi-incurved decorative. |

NOTE.—Comparisons made of plants grown in a greenhouse in Barberton, Ohio under conditions as described in Chart A and Chart B.

We claim:

1. A new and distinct cultivar of chrysanthemum plant characterized particularly by the combined characteristics of decorative inflorescence type and flat inflorescence form, 4 to 5.5 inches diameter across face of inflorescence at maturity, uniform eight week flowering response, short plant height, semi-upright branching habit, and its adaptability due to responsiveness of height to daylength and B–9.

No references cited.

ROBERT E. BAGWILL, Primary Examiner